(12) United States Patent
Tang

(10) Patent No.: US 6,409,718 B1
(45) Date of Patent: Jun. 25, 2002

(54) DEVICE AND METHOD FOR CORRECTING ASTIGMATISM BY LASER ABLATION

(75) Inventor: Fuqian Tang, Orlando, FL (US)

(73) Assignee: LaserSight Technologies, Inc., Winter Park, FL (US)

( * ) Notice: Subject to any disclaimer, the term of this patent is extended or adjusted under 35 U.S.C. 154(b) by 0 days.

(21) Appl. No.: 09/017,680

(22) Filed: Feb. 3, 1998

(51) Int. Cl.[7] .............................................. A61B 18/18
(52) U.S. Cl. .............................. 606/5; 606/4; 128/898
(58) Field of Search ........................... 606/4, 5, 6, 10, 606/11, 12; 128/898

(56) References Cited

U.S. PATENT DOCUMENTS

| | | |
|---|---|---|
| 2,480,737 A | 8/1949 | Jayle |
| 3,074,407 A | 1/1963 | Moon |
| 3,476,112 A | 11/1969 | Elstein |
| 3,697,889 A | 10/1972 | Dewey, Jr. |
| 3,743,965 A | 7/1973 | Offner |
| 3,848,104 A | 11/1974 | Locke |
| 3,938,058 A | 2/1976 | Yamamoto |
| 3,982,541 A | 9/1976 | L'Esperance, Jr. |
| 3,983,507 A | 9/1976 | Tang et al. |
| 4,169,663 A | 10/1979 | Murr |

(List continued on next page.)

FOREIGN PATENT DOCUMENTS

| | | |
|---|---|---|
| CA | 1243732 | 10/1984 |
| EP | 0 151869 A1 | 8/1985 |
| EP | 0296982 A1 | 6/1988 |
| EP | 0151869 B1 | 1/1990 |

(List continued on next page.)

OTHER PUBLICATIONS

D. Eimerl, L. Davis, & S. Vlesko, Optical, mechanical, and thermal properties of barium borate, Journal of Applied Physics, Sep. 1987, pp. 1968–1983.

J.T. Lin, Non–linear crystals for tunable coherent sources, Optical and Quatum Electronics, 1990, pp. S283–S313.

J.T. Lin, Temperature–tuned noncritically phase–matched frequency conversion in LiB305 crystal, Optics Communications, Dec. 1990, pp. 159–165.

Y. Tanaka, H. Kuroda, & S. Shionoya, Generation of Tunable Picsecond Pulses in the Ultraviolet Region Down to 197nm, May, 1982, pp. 434–436.

*Primary Examiner*—Linda C. M. Dvorak
*Assistant Examiner*—A. Farah
(74) *Attorney, Agent, or Firm*—William H. Bollman

(57) ABSTRACT

A method for correction of a simple astigmatism of a corneal surface of an eye is provided. The method provides a laser operable to produce a pulsed output laser beam. A scanning mechanism is positioned to operatively receive the pulsed output laser beam of the laser and operable to control the scanning of the pulsed output laser beam over a target surface to be ablated. A computer system is operatively connected to the scanning mechanism for control thereof with the computer system operable to determine a desired configuration of an ablation to be performed on the target surface and to define a boundary associated with the ablation. The computer system is further operable to determine the number of layers required to be ablated to achieve the desired configuration of the ablation and a boundary and a scanning pattern associated with each layer with the computer system and the scanning mechanism operable with one another to ablate the target surface in a series of layers the number of which corresponds to the number determined such that the resultant ablation on the target surface corrects the simple astigmatism.

4 Claims, 7 Drawing Sheets

U.S. PATENT DOCUMENTS

| | | |
|---|---|---|
| 4,180,751 A | 12/1979 | Ammann |
| 4,349,907 A | 9/1982 | Campillo et al. |
| 4,386,428 A | 5/1983 | Baer |
| 4,423,728 A | 1/1984 | Lieberman |
| 4,461,294 A | 7/1984 | Baron |
| 4,477,159 A | 10/1984 | Mizuno et al. |
| 4,520,816 A | 6/1985 | Schachar et al. |
| 4,526,171 A | 7/1985 | Schachar |
| 4,538,608 A | 9/1985 | L'Esperance, Jr. |
| 4,546,773 A | 10/1985 | Kremer et al. |
| 4,573,467 A | 3/1986 | Rich et al. |
| 4,580,559 A | 4/1986 | L'Esperance, Jr. |
| 4,598,714 A | 7/1986 | Kremer et al. |
| 4,619,259 A | 10/1986 | Graybill et al. |
| 4,633,866 A | 1/1987 | Peyman et al. |
| 4,638,801 A | 1/1987 | Daly et al. |
| 4,653,495 A | 3/1987 | Nanaumi |
| 4,662,370 A | 5/1987 | Hoffman et al. |
| 4,665,913 A | 5/1987 | L'Esperance, Jr. |
| 4,669,466 A | 6/1987 | L'Esperance |
| 4,688,570 A | 8/1987 | Kramer et al. |
| 4,718,418 A | 1/1988 | L'Esperance, Jr. |
| 4,720,189 A | 1/1988 | Heyman et al. |
| 4,721,379 A | 1/1988 | L'Esperance, Jr. |
| 4,729,372 A | 3/1988 | L'Esperance, Jr. |
| 4,729,373 A | 3/1988 | Peyman |
| 4,732,148 A | 3/1988 | L'Esperance, Jr. |
| 4,764,930 A | 8/1988 | Bille et al. |
| 4,770,172 A | 9/1988 | L'Esperance |
| 4,773,414 A | 9/1988 | L'Esperance, Jr. |
| 4,784,135 A | 11/1988 | Blum et al. |
| 4,798,204 A | 1/1989 | L'Esperance, Jr. |
| 4,807,623 A | 2/1989 | Lieberman |
| 4,838,266 A | 6/1989 | Koziol et al. |
| 4,838,679 A | 6/1989 | Bille |
| 4,840,175 A | 6/1989 | Peyman |
| 4,848,340 A | 7/1989 | Bille et al. |
| 4,856,513 A | 8/1989 | Muller |
| 4,862,886 A | 9/1989 | Clarke et al. |
| 4,896,015 A | 1/1990 | Taboada et al. |
| 4,903,695 A | 2/1990 | Warner et al. |
| 4,907,586 A | 3/1990 | Bille et al. |
| 4,911,711 A | 3/1990 | Telfair et al. |
| 4,925,523 A | 5/1990 | Braren et al. |
| 4,941,093 A | 7/1990 | Marshall et al. |
| 4,968,130 A | 11/1990 | Hideshima et al. |
| 4,975,918 A | 12/1990 | Morton |
| 4,993,826 A | 2/1991 | Yoder |
| 4,994,058 A | 2/1991 | Raven et al. |
| 5,019,074 A | 5/1991 | Muller |
| 5,052,004 A | 9/1991 | Gratze et al. |
| 5,063,942 A | 11/1991 | Kilmer et al. |
| 5,065,046 A | 11/1991 | Guyer |
| 5,074,859 A | 12/1991 | Koziol |
| 5,102,409 A | 4/1992 | Balgorod |
| 5,108,388 A | 4/1992 | Trokel |
| 5,108,412 A | 4/1992 | Krumeich et al. |
| 5,133,726 A | 7/1992 | Ruiz et al. |
| 5,144,630 A | 9/1992 | Lin |
| 5,163,934 A | 11/1992 | Munnerlyn |
| 5,163,936 A | 11/1992 | Black et al. |
| 5,182,759 A | 1/1993 | Anthon et al. |
| 5,188,631 A | 2/1993 | L'Esperance, Jr. |
| 5,196,006 A | 3/1993 | Klopotek et al. |
| 5,207,668 A | 5/1993 | L'Esperance, Jr. |
| 5,217,452 A | 6/1993 | O'Donnell |
| 5,219,343 A | 6/1993 | L'Esperance, Jr. |
| 5,219,344 A | 6/1993 | Yoder, Jr. |
| 5,222,960 A | 6/1993 | Poley |
| 5,226,903 A | 7/1993 | Mizuno |
| 5,250,062 A | 10/1993 | Hanna |
| 5,257,988 A | 11/1993 | L'Esperance, Jr. |
| 5,263,950 A | 11/1993 | L'Esperance, Jr. |
| 5,284,477 A * | 2/1994 | Hanna et al. .................. 606/5 |
| 5,288,292 A | 2/1994 | Giraud et al. |
| 5,290,301 A | 3/1994 | Lieberman |
| 5,312,320 A | 5/1994 | L'Esperance, Jr. |
| 5,324,281 A | 6/1994 | Muller |
| 5,334,190 A | 8/1994 | Seiler |
| 5,336,217 A | 8/1994 | Buys et al. |
| 5,345,534 A | 9/1994 | Najm et al. |
| 5,349,590 A | 9/1994 | Amirkhanian et al. |
| 5,350,374 A | 9/1994 | Smith |
| 5,353,262 A | 10/1994 | Yakymyshyn et al. |
| 5,360,424 A | 11/1994 | Klopotek |
| 5,363,388 A | 11/1994 | Shi et al. |
| 5,364,388 A | 11/1994 | Koziol |
| 5,370,641 A | 12/1994 | O'Donnell, Jr. |
| 5,395,356 A * | 3/1995 | King et al. .................... 606/4 |
| 5,395,362 A | 3/1995 | Sacharoff et al. |
| 5,405,355 A | 4/1995 | Peyman et al. |
| 5,411,501 A | 5/1995 | Klopotek |
| 5,423,801 A | 6/1995 | Marshall et al. |
| 5,425,727 A | 6/1995 | Koziol |
| 5,425,729 A | 6/1995 | Ishida et al. |
| 5,437,658 A | 8/1995 | Muller et al. |
| 5,441,511 A | 8/1995 | Hanna |
| 5,442,487 A | 8/1995 | Mizuno |
| 5,445,633 A | 8/1995 | Nakamura et al. |
| 5,461,212 A | 10/1995 | Seiler et al. |
| 5,470,329 A | 11/1995 | Sumiya |
| 5,474,548 A | 12/1995 | Knopp et al. |
| 5,480,396 A | 1/1996 | Simon et al. |
| 5,505,723 A | 4/1996 | Muller |
| 5,507,741 A | 4/1996 | L'Esperance, Jr. |
| 5,507,799 A | 4/1996 | Sumiya |
| 5,520,679 A * | 5/1996 | Lin .............................. 606/5 |
| 5,549,597 A | 8/1996 | Shimmick et al. |
| 5,556,395 A | 9/1996 | Shimmick et al. |
| 5,571,107 A * | 11/1996 | Shaibani et al. ............... 606/4 |
| 5,582,752 A | 12/1996 | Zair |
| 5,599,340 A | 2/1997 | Simon et al. |
| 5,613,965 A | 3/1997 | Muller |
| 5,624,436 A | 4/1997 | Nakamura et al. |
| 5,634,920 A * | 6/1997 | Hohla ......................... 606/12 |
| 5,637,109 A | 6/1997 | Sumiya |
| 5,646,791 A | 7/1997 | Glockler |
| 5,651,784 A | 7/1997 | Klopotek |
| 5,683,379 A | 11/1997 | Hohla |
| 5,684,562 A | 11/1997 | Fujieda |
| 5,711,762 A | 1/1998 | Trokel |
| 5,713,892 A | 2/1998 | Shimmick |
| 5,735,843 A | 4/1998 | Trokel |
| 5,782,822 A * | 7/1998 | Telfair et al. .................. 606/5 |
| 5,849,006 A | 12/1998 | Frey et al. |
| 5,865,830 A | 2/1999 | Parel et al. |
| 5,997,529 A * | 12/1999 | Tang et al. .................... 606/4 |
| 6,010,497 A * | 1/2000 | Tang et al. .................... 606/5 |
| 6,090,100 A * | 7/2000 | Hohla .......................... 606/5 |
| 6,190,374 B1 * | 2/2001 | Amano et al. .................. 606/5 |
| 6,203,539 B1 * | 3/2001 | Shimmick et al. ............. 606/5 |
| 6,319,247 B1 * | 11/2001 | Hofer et al. ................... 606/5 |

FOREIGN PATENT DOCUMENTS

| | | |
|---|---|---|
| EP | 0368512 A2 | 5/1990 |
| EP | 0207648 B1 | 8/1990 |

| | | | | | |
|---|---|---|---|---|---|
| EP | 0418890 A3 | 3/1991 | WO | PCT/US94/02007 | 9/1994 |
| EP | 0602756 A1 | 6/1994 | WO | PCT/EP95/01287 | 10/1995 |
| WO | PCT/FR87/00139 | 11/1987 | | | |
| WO | PCT/US92/09625 | 5/1993 | * cited by examiner | | |
| WO | PCT/US93/00327 | 8/1993 | | | |

DEVICE AND METHOD FOR CORRECTING ASTIGMATISM BY LASER ABLATION

BACKGROUND OF THE INVENTION

1. Field of the Invention

The present invention relates to a device and method for reshaping a corneal surface of an eye for refractive correction by laser ablation. More particularly, it relates to an improved device and method for corneal reshaping by laser ablation for correcting a simple astigmatism condition.

2. Description of Related Art

While many people have perfect eyesight, many others do not. One reason for imperfect eyesight is caused by refractive disorders of the eye. Astigmatism is one possible refractive disorder of the eye caused by an out-of-round cornea. Astigmatism results in light from a point source being focused in an image line rather than a point.

One method of treating simple astigmatism is through the use of conventional laser refractive surgery. Laser refractive surgery utilizes a laser to ablate and thus remove layers of corneal tissue in a predetermined pattern to correct the refractive disorder. Typically, such laser refractive surgery ablates many layers of corneal tissue with the cumulative effect attempting to form, e.g., a narrow, cylinder-shaped portion removed from the cornea. However, conventional apparatus and method only approximate removal of a cylinder-like portion, and a smooth surface on the remaining corneal tissue is often difficult to achieve, leading to problems of clarity of eye sight.

It is known to ablate or remove a narrow, cylinder-shaped portion from the corneal surface of the eye to correct this particular eye disorder, as illustrated in FIGS. 2a–2c. FIG. 2a depicts the ideal surface of the cornea after a narrow, cylinder-shaped portion is removed. FIGS. 2b and 2c show the ideal surface of the cornea in cross section along the x-axis and y-axis, respectively.

Ideally, this correction corrects astigmatism. Unfortunately, the real world is less than ideal. For instance, FIG. 2d depicts the actual surface of the cornea in cross section along the y-axis resulting from conventional laser refractive surgery methods and apparatus. The sharp, ideal corners 200 of the ablated area are actually somewhat rounded. Moreover, although substantially flat after initial ablation, cylindrical correction of simple astigmatism is known to induce hyperopia, another refractive disorder of the eye, along, e.g., the flat or y-axis, as illustrated in FIG. 2e. The induced hyperopia is caused by corneal re-growth or regression after the laser refractive surgery away from the corneal surface 202 initially after ablation.

Furthermore, certain conventional laser refractive surgeries utilizing a small, low-energy laser beam scan, each corneal tissue layer is ablated by a large number of equally spaced laser pulses with each laser pulse partially overlapping adjacent laser pulses. Unfortunately, in a small, low-energy laser is beam scan, the first laser beam scan and the last laser beam scan do not always fall on the pre-defined border of the ablation zone of a particular corneal tissue layer.

For example, FIG. 4 depicts a conventional method of scanning an ablating laser beam across a generally rectangular ablation zone. As shown, the ablation points may or may not be centered on a predetermined border 402. For instance, although the ablation points 404 may be centered on the starting border 406, the last ablation points in a series of scan lines may not be centered on the ending border 402.

Thus, by not knowing where the starting point and/or ending point will land, the eye surgeon has a difficult time achieving an accurate layer width and centration in scanning ablation.

Lastly, since the cylindrical ablation is usually narrow, the total depth of ablation is typically small, and therefore the number of corneal tissue layers to be ablated is small. The typical thickness of a layer of corneal tissue is approximately two (2) micrometers ($\mu$m), and because the number of corneal tissue layers to be ablated is typically small, the effectiveness of the procedure is generally impacted. A small number of layers causes inaccuracy of total depth of ablation because each layer of the few layers represents a reasonably large percentage of the total depth to be ablated. For example, if three and one-half (3.5) layers at two (2) $\mu$m each are required to be ablated to result in a total depth of seven (7) $\mu$m, the eye surgeon must choose between an ablation of either three (3) layers or four (4) layers, since it is not feasible to ablate only half a corneal tissue layer. By ablating either three (3) layers or four (4) layers instead of the ideal 3.5 layers, significant error is caused in the ablation, i.e., approximately fourteen (14%) percent, and thus the refractive disorder may not be completely corrected.

Accordingly, there exists a need for an improved device and method for correcting simple astigmatism by laser ablation which obviates and overcomes many of the disadvantages and shortcomings experienced with the prior laser surgery devices. For instance, there is a need for an improved device and method for correcting simple astigmatism by laser ablation which does not induce hyperopia. Furthermore, there is a need to correct simple astigmatism by laser ablation more accurately along a predefined border of the ablation zone. Lastly, there is a need to improve the inherent error otherwise caused in the ablation of a small number of corneal tissue layers.

SUMMARY OF THE INVENTION

In accordance with the principles of one aspect of the present invention, astigmatism is corrected with apparatus comprising an ablating pulsed laser beam, and a scanner to scan the ablating pulsed laser beam in scan paths across an ablation zone of the eye. A rotator rotates an angle of the scan paths with respect to the ablation zone based on a step size between pulses of the ablating pulsed laser beam.

A method of scanning a laser beam across an ablation zone of an eye is also provided. According to the method, a total number of ablation layers to perform a particular refractive correction of the eye are determined. An approximate step size between each ablation point in scan lines across the ablation zone is determined. A rotation of the scan lines with respect to the ablation zone based on at least one of the total number of ablation layers and the approximate step size is determined, and the laser beam is scanned in a predetermined pattern based on the rotation of the scan lines.

In accordance with another aspect of the present invention, apparatus is provided for forming a cylindrical-shaped ablation in a cornea of an eye. The apparatus comprises an ablating pulsed laser beam, and a scanner to scan the ablating pulsed laser beam in a plurality of scan paths across an ablation zone of the eye to remove a plurality of layers of corneal tissue. The scanner progressively decreases the lengths from a first to last one of the plurality of layers.

In accordance with another method of the present invention, astigmatism is corrected in an eye by scanning an ablating laser beam in a predetermined pattern across an ablation zone of the eye to form a cylindrical-shaped ablation in a cornea of the eye. Moreover, a transition region is further ablated in each end of the cylindrical-shaped ablation.

In accordance with yet another aspect of the invention, astigmatism is corrected in an eye by identifying a center of a refractive correction in the eye, and a rectangular ablation zone is determined about the center. A maximum depth of ablation is determined, and a total number of ablation layers corresponding to said maximum depth is determined. A scanning pattern is determined for each of the ablation layers, with each of the scanning patterns including a step size between pulses of an ablating laser based on the desired total number of ablation layers. Each of the ablation layers is then ablated with the respectively determined scanning patterns.

BRIEF DESCRIPTION OF THE DRAWINGS

Features and advantages of the present invention will become apparent to those skilled in the art from the following description with reference to the drawings, in which:

FIG. 2b is a cross-sectional view along the x-axis of the prior art narrow, cylinder-like ablation on a corneal surface of an eye according to the prior art as illustrated in FIG. 2a;

FIG. 2c is a cross-sectional view along the y-axis of the prior art narrow, cylinder-like ablation on a corneal surface of an eye according to the prior art as illustrated in FIG. 2a;

FIG. 2d is a cross-sectional view along the y-axis of the prior art narrow, cylinder-like ablation on a corneal surface of an eye illustrating the flat corneal surface initially after ablation according to the prior art as illustrated in FIG. 2a;

FIG. 2e is a cross-sectional view along the y-axis of the prior art narrow, cylinder-like ablation on a corneal surface of an eye illustrating the curved corneal surface after tissue growth or regression according to the prior art as illustrated in FIG. 2a;

FIG. 3b is a cross-sectional view along the x-axis of the present invention cylinder-like ablation of corneal tissue according to the present invention as illustrated in FIG. 3a;

FIG. 3c is a cross-sectional view along the y-axis of the present invention cylinder-like ablation of corneal tissue according to the present invention as illustrated in FIG. 3a;

FIG. 3d is a cross-sectional view along the y-axis of the present invention cylinder-like ablation of corneal tissue illustrating the flat corneal surface initially after ablation according to the present invention as illustrated in FIG. 3a;

FIG. 3e is a cross-sectional view along the y-axis of the present invention cylinder-like ablation of corneal tissue illustrating the flat corneal surface after tissue growth or regression according to the present invention as illustrated in FIG. 3a;

DETAILED DESCRIPTION OF THE ILLUSTRATIVE EMBODIMENT

In accordance with the principles of the present invention, simple astigmatism is correctable by more accurately re-profiling the surface of the cornea of an eye by ablating a substantially cylindrical-like portion of the corneal surface. For instance, the present invention provides apparatus and a method to suppress, prevent or eliminate the inducement of hyperopia, to more accurately ablate along a predetermined border of an ablation zone, and to more accurately ablate a predetermined depth.

Figure 1:
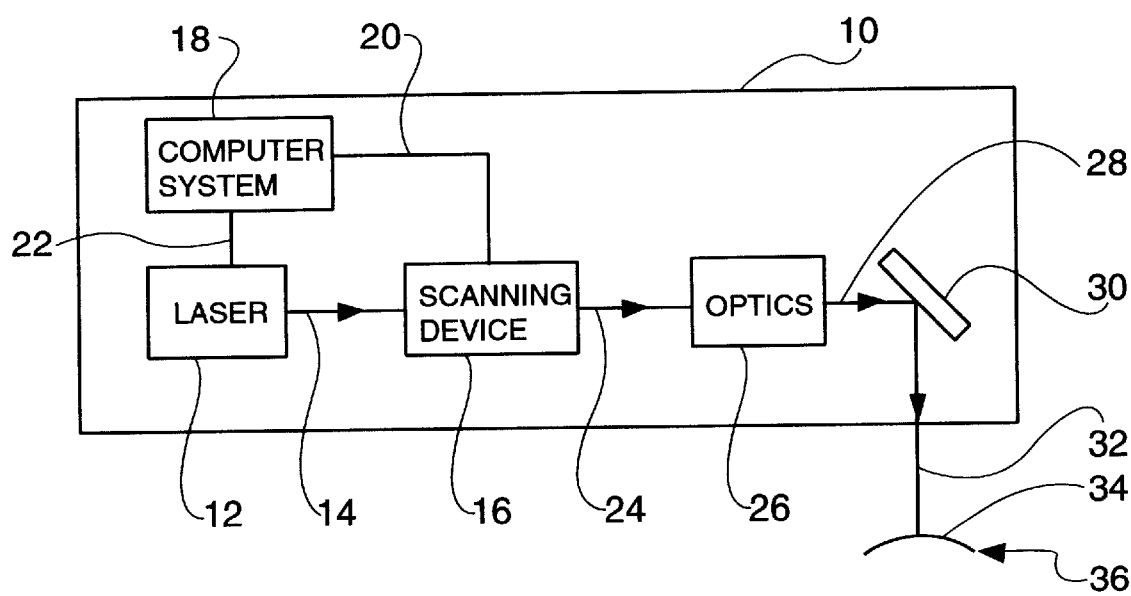
FIG. 1 is a diagrammatic view illustrating a device for re-profiling the surface an eye constructed in accordance with the present invention.

One embodiment of a laser device in accordance with the principles of the present invention is shown in FIG. 1.

In FIG. 1, a laser device 10 includes a laser 12 operable to produce a pulsed output laser beam 14, which is directed to a scanning device 16. The scanning device 16 is operatively connected to a computer system 18 for control thereby. The computer system 18 can be located within the laser device 10. The laser 12 can also be operatively connected to the computer system 18 for control thereby.

The scanning device 16 of the laser device 10 of the present invention is operable to control the scanning of the pulsed output laser beam 14 across a target area on the cornea 34 of the patient's eye 36. A scanned laser beam 24 departs the scanning device 16 and is directed to other optics components 26 which may be utilized for shaping the scanned beam 24 in a desired manner. A shaped scanned beam 28 may then be directed to a reflecting mirror 30, and a reflected beam 32 is directed from the reflecting mirror 30 onto a cornea 34 of a patient's eye 36.

The various portions of the laser device 10 can be constructed in accordance with the laser device described in U.S. Pat. No. 5,520,679, the disclosure of which is hereby explicitly incorporated herein by reference.

Figure 3A:
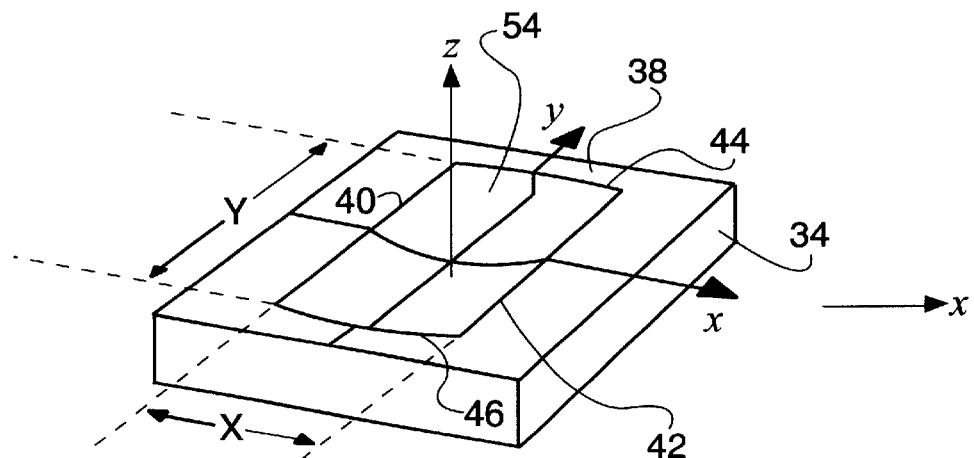
FIG. 3a illustrates a section of a corneal surface of an eye having a cylinder-like ablated portion according to the present invention, which ablated portion is representative of the ablation desirable to successfully treat a simple astigmatic disorder.

FIG. 3a shows a more accurate cylindrical-shaped ablation 38 performed in accordance with the present invention, with reference to x-, y- and z-axes.

The cylindrical-shaped ablation 38 in accordance with the principles of the present invention generally includes opposing sides 40 and 42 defining the width of the cylindrical-shaped ablation 38 illustrated by a distance X, and opposing ends 44 and 46 defining the length of the ablation 38 and illustrated by a distance Y.

Figure 3B:
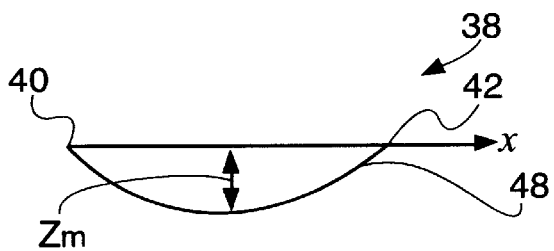

FIG. 3b shows a cross-sectional view of the cylindrical-shaped ablation along the x-axis shown in FIG. 3a. The cylindrical-shaped ablation 38 is termed "cylindrical-shaped" or "cylindrical-like" in that the corneal surface 48 remaining after ablation, from side 40 to side 42, is generally circumferential in nature. The maximum depth of the ablation $Z_m$ is generally located along a central, lengthwise line of the cylindrical-shaped ablation 38.

The dimensions X and Y define a rectangular zone 54 which is centered at the origin of the x-, y-, and z-axes. Once the depth $Z_m$ is conventionally determined, the number of corneal tissue layers needed to be ablated is calculated. The corneal tissue layers are individually ablated until all the required layers have been removed from the cornea 34 to form the cylindrical-shaped ablation 38.

Figure 3C:
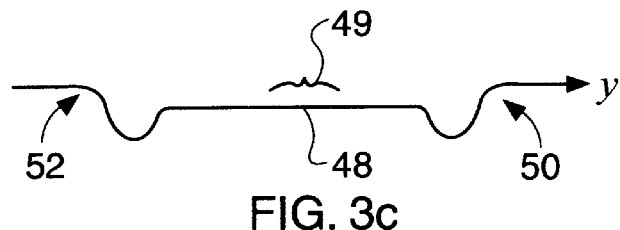

FIG. 3c shows a cross-sectional view of the cylindrical-shaped ablation 38 along the y-axis in accordance with the principles of the present invention.

In FIG. 3c, transition regions 50 and 52 are formed in the corneal surface near the lengthwise ends 44, 46 of the cylindrical-shaped ablation 38. The transition regions 50, 52 have an additional depth with respect to a central portion 49 of the ablated corneal surface.

The depth and width of the additional ablation at the transition regions 50, 52 is based on the regression rate, the age of the patient, and other factors otherwise inducing the disadvantageous hyperopic condition as in conventional methods and apparatus. The additional depth of the transition regions 50, 52 is preferably achieved by alternatively ablating the cornea 34 at the transition regions 50 and 52 after the ablation of each corneal tissue layer, after every two corneal tissue layers, after every three corneal tissue layers, etc. The transition regions 50, 52 can alternatively be ablated in the beginning, at the end, or in the middle of the performance of the overall ablation profile determined by the math model.

Figure 3D:
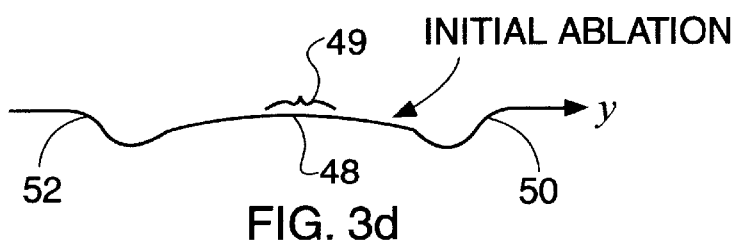
Figure 3E:
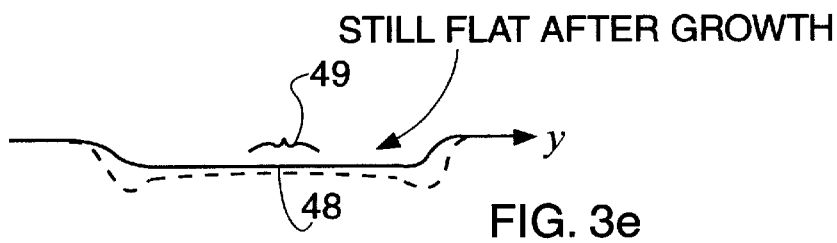
Figure 4:
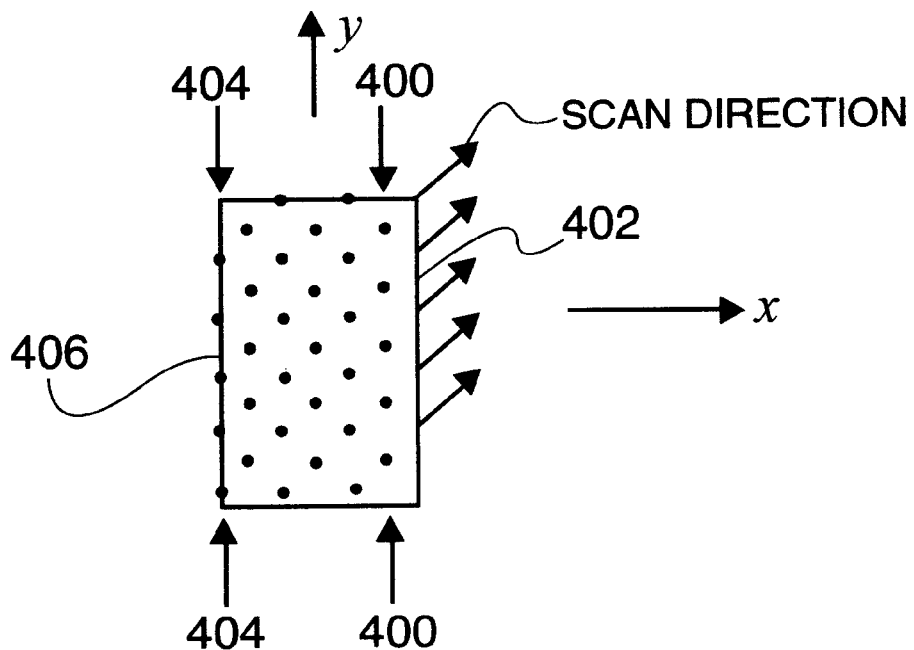
FIG. 4 is a top plan view illustrating a laser pulse spacing utilized for laser refractive correction according to the prior art in which the laser pulses are not positioned on the ending boundary of the layer.

FIG. 3d depicts the corneal surface after initial ablation, and FIG. 3e depicts the corneal surface after re-growth and regression. As illustrated in FIGS. 3d and 3e, the additional depth in the cylindrical-shaped ablation 38 at the transition regions 50, 52 in accordance with the principles of the present invention maintains a flatness in the corneal surface 48, particularly in the central portion 49, after corneal tissue growth or regression.

Figure 2A:
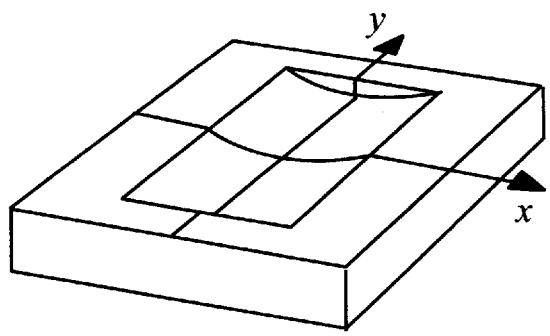
FIG. 2a illustrates a section of a corneal surface of an eye having a narrow, cylinder-like ablation according to the prior art.
Figure 2B:
Figure 2C:
Figure 2D:
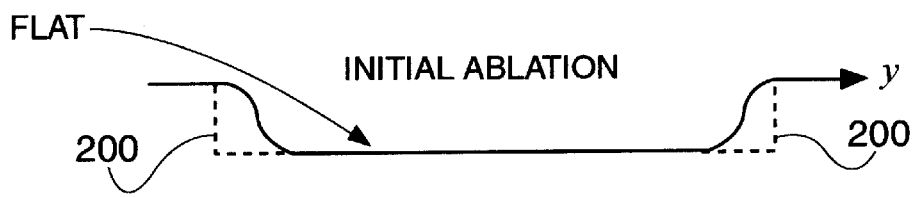
Figure 2E:
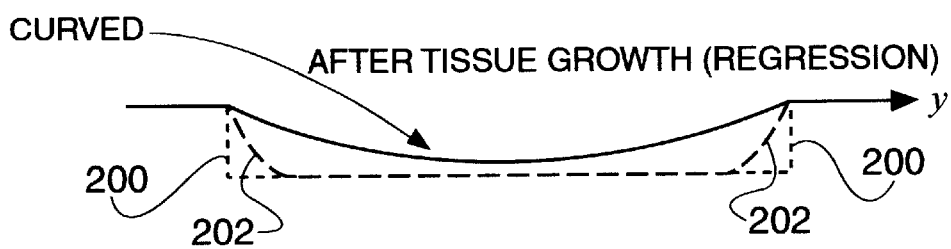

Unlike the disadvantages of conventional apparatus and methods with respect to the initial flat ablation surface becoming curved causing hyperopia after corneal tissue re-growth or regression (as shown in FIGS. 2d and 2e), the present invention provides an ablation including initially deeper transition regions 50, 52 to prevent or counteract the effects of re-growth or regression. As a result of the transition regions 50, 52, the ablation surface 48 remains substantially flat after re-growth and/or regression, suppressing, preventing, and/or compensating for any induced hyperopia.

In accordance with another aspect of the present invention, it is determined that to increase accuracy in laser ablation, it is generally preferred to increase the total number of ablated layers while reducing the number of ablation pulses per layer. However, a reduction in the number of ablation pulses per layer decreases the accuracy in ablation of a border of an ablation zone.

The present invention provides an improved accuracy in laser ablation methods and apparatus such that both starting and ending laser ablation points in scan lines across an ablation zone will be substantially centered on both a starting and an ending border, thus allowing the spacing between laser ablation points to be increased and the total number of layers to be increased to provide a smoother and more accurate total ablation depth.

Figure 5:
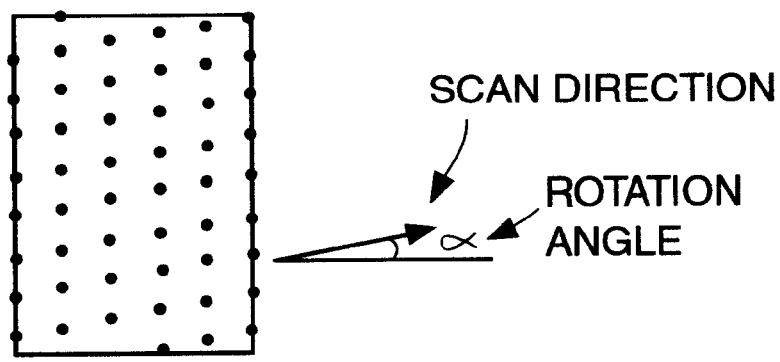
FIG. 5 is a top plan view illustrating a preferred laser pulse spacing in accordance with the present invention in which the laser pulses are positioned on the starting and ending boundaries of the layer.

After the total number of layers to be ablated is determined, a scanning ablation pattern for each of the layers may be determined. FIG. 5 shows an ablation layer with a scanning pattern having a rotation corresponding to an angle α determined in accordance with the principles of the present invention. FIGS. 6A to 6D illustrate in more detail the scanning ablation patterns for four sequential layers, each having an angle calculated in accordance with this aspect of the present invention.

Figure 6A:
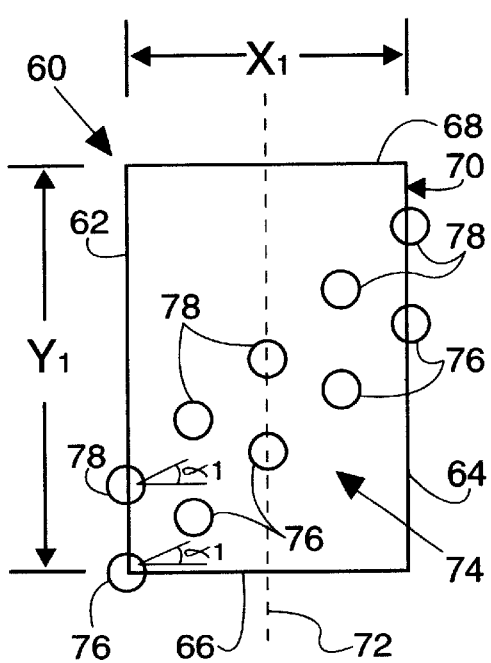
FIGS. 6A through 6D illustrate a series of layers to be ablated in accordance with the present invention in order to correct a simple astigmatic disorder, each layer including a boundary and a preferred partial scanning pattern of pulses associated therewith.

In FIG. 6A, a first ablation layer 60 is defined by a pair of opposing sides 62 and 64 defining the width of the ablation layer 60 illustrated by a distance $X_1$, and opposing ends 66 and 68 defining the length of the layer 60 illustrated by a distance $Y_1$. The width $X_1$ and the length $Y_1$ define a rectangular zone 70 having an axis of symmetry represented by the dashed line 72. The rectangular zone 70 is also the boundary of the layer 60.

FIG. 6A also illustrates an exemplary scanning pattern 74 associated therewith and determined in accordance with the principles of the present invention. The scanning pattern 74 includes laser pulses 76 and 78. The lasers pulses 76 and 78 start and end on a boundary 70 of the layer 60. For example, laser pulses 76 start on the side 62 and end of the side 64. The laser pulses 78 also start on the side 62 and also end on the side 64. In accordance with the present invention, the scan lines are rotated from a horizontal position, i.e., corresponding to an angle $\alpha_1$ from the horizontal, for a scanning pattern 74 is selected such that, based on a predetermined distance between laser pulses 76, 78, the starting and ending pulses will lie on the boundary 70 of the layer 60.

Since the distance between the pulses 76 and 78 are fixed and the width $X_1$ and the length $Y_1$ are known, a rotation angle $\alpha_1$ can be calculated that will allow the starting and ending pulses to lie on the boundary 70 of the layer 60. The rotation angle $\alpha_1$ satisfies the condition $\alpha_1 = \cos^{-1}(w_n / m \times \delta)$ where $w_n$ is the width of the nth layer under consideration, δ is the scan step size, and m is any integer number. This will result in a symmetric distribution of the pulses 76 and 78 about the axis 72 which forces all of the pulses 76 and 78 to be centered about the axis 72.

The rotation angle $\alpha_1$ can be restricted in a variety of ways by varying the integer m. The rotation angle $\alpha_1$ may be restricted to within a certain range, e.g., alternatively selecting a rotation angle $\alpha_1$ between 0° and 90° for even numbered layers, and a rotation angle $\alpha_1$ between 90° and 180° for odd numbered layers. An alternative method to restrict the rotation angle $\alpha_1$ is to select a rotation angle $\alpha_1$ having the lowest value for the integer m.

According to conventional methods and apparatus, without the immediately described angular adjustment of the scanning pattern 74, accuracy could only be increased by decreasing the step size such that, by chance, the last scan points in most scan lines would ablate corneal tissue sufficiently close to the ending border. While increasing accuracy, increasing the step size disadvantageously lengthens the surgical procedure and increases the amount of corneal tissue ablated in each layer. According to the principles of this aspect of the present invention, the rotation angle $\alpha_1$ of the scanning pattern 74 is calculated for each layer ablated to cause an ablation point in each scanned line to be substantially centered on both a starting and an ending border of the ablation zone. Thus, because the borders of the ablation zone can be ablated with accuracy, the spacing between the ablation points can be increased to allow a higher number of ablation patterns to be performed, thus further increasing the accuracy in the depth of the overall ablation.

One major benefit to increasing the spacing between pulses and increasing the number of ablation layers in accordance with the principles of the present invention is that the conventional error associated with a small total number of ablation layers is reduced significantly. For example, due to inherent hardware limitations of a laser system, directly ablating half a corneal tissue layer is not feasible. Therefore, if it is determined that one and one-half (1.5) layers of the surface of the cornea have to be ablated in order to correct the vision of the patient, then the best the laser system can do is to ablate either one (1) layer or two (2) layers resulting in an error of 33.33%. However, by substantially doubling the spacing between pulses in accordance with the method of the present invention, which also increases the number of layers to be ablated, the error associated with any system limitations will substantially decrease. By way of example, under the previous known method whereby one and one-half (1.5) layers were calculated, by doubling the spacing of the pulses in accordance with the present invention, the calculated one and one-half (1.5) layers is equivalent to six and one-half (6.5) layers. Again, because half of a layer cannot be ablated, either six (6) or seven (7) layers must be ablated. This results in an error of only about 7.7% which is much more acceptable than the error of 33.33%.

Of course, the step size can be increased by any amount, e.g., 1.5, 2.5, 3, etc. Furthermore, instead of increasing both the scan step size and the distance between scanned lines, either the scan step size or the distance between scanned lines can be increased to increase accuracy in accordance with the principles of the present invention.

Thus, in accordance with this aspect of the present invention, as shown in FIG. 6A, the rotation angle $\alpha_1$ of the scanning pattern 74 is adjusted such that pulses 76 and 78 start and end on the boundary 70, even with an increased step size and/or increased distance between scanned lines.

Only portions of the entire scanning patterns are shown in FIGS. 6A to 6D for illustration purposes only. It is to be understood by those of skill in the art that other pulses (not shown) are also used in ablating the layers.

Figure 6B:
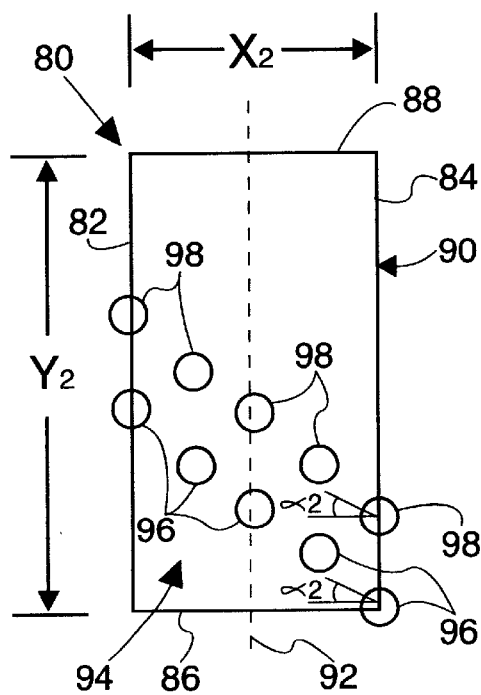

FIG. 6B shows a second ablation layer 80 having a pair of opposing sides 82 and 84 defining the width of the ablation layer 80 illustrated by a distance $X_2$, and opposing ends 86 and 88 defining the length of the layer 80 illustrated by a distance $Y_2$. The width $X_2$ and the length $Y_2$ define a rectangular zone 90 having an axis of symmetry represented by the dashed line 92. The rectangular zone 90 is also the boundary of the layer 80.

FIG. 6B further illustrates a second scanning pattern 94 associated with the second ablation layer 80 chosen in accordance with the principles of the present invention. The second scanning pattern 94 includes laser pulses 96 and 98. The lasers pulses 96 and 98 start and end on the boundary 90 of the second ablation layer 80. For example, laser pulses 96 start on the side 84 and end of the side 82. The laser pulses 98 also start on the side 84 and also end on the side 82. In accordance with the principles of this aspect of the present invention, a rotation angle $\alpha_2$ is calculated such that the starting and ending pulses of each or substantially each scan line lie on the boundary 90 of the layer 80, based on a desired distance between the pulses 96 and 98, the width $X_2$ and the length $Y_2$. Once again, this will result in a symmetric distribution of the pulses 96 and 98 about the axis 92.

The scanning pattern 94 represented by the pulses 96 and 98 illustrated in FIG. 6B may begin and end in a direction opposite that shown in FIG. A, as shown in FIG. 6B. Additionally, the width $X_2$ of the second ablation layer 80 may be less than the width $X_1$ of the first ablation layer 60, and the length $Y_2$ of the second ablation layer 80 may be greater than the width $Y_1$ the first ablation layer 60.

Figure 6C:
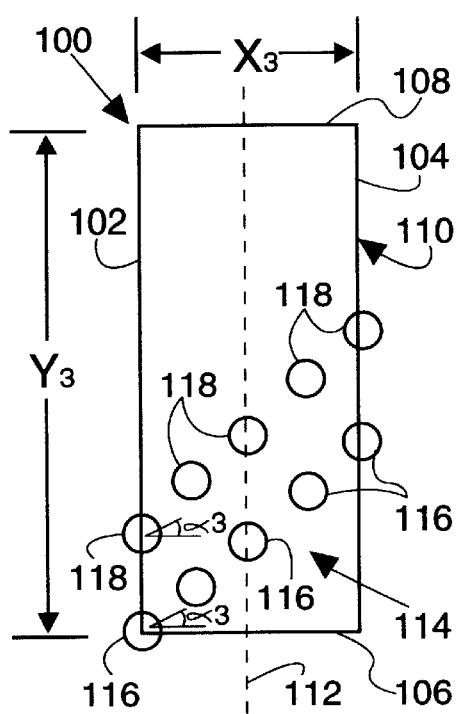

FIG. 6C shows a third ablation layer 100 having a pair of opposing sides 102 and 104 defining the width $X_3$ of the third ablation layer 100, and opposing ends 106 and 108 defining the length $Y_3$ of the third ablation layer 100. The width $X_3$ and length $Y_3$ define a rectangular zone 110 having an axis of symmetry illustrated by the dashed line 112. The rectangular zone 110 is also the boundary of the third ablation layer 100.

FIG. 6C also illustrates a third scanning pattern 114 determined for the third ablation layer 100. The third scanning pattern 114 includes laser pulses 116 and 118. The lasers pulses 116 and 118 start and end on the boundary 110 of the third ablation layer 100. For example, laser pulses 116 start on the side 102 and end of the side 104. The laser pulses 118 also start on the side 102 and also end on the side 104. Since the distance between the pulses 116 and 118 are fixed and the width $X_3$ and the length $Y_3$ are known, a rotation angle $\alpha_3$ can be calculated in accordance with the principles of this aspect of the present invention such that the starting and ending pulses can be caused to lie if substantially on the boundary 110 of the third ablation layer 100. This will result in a symmetric distribution of the pulses 116 and 118 about the axis 112 which forces all of the pulses 116 and 118 to be centered about the axis 112.

The third scanning pattern 114 represented by the pulses 116 and 118 illustrated in FIG. 6C may begin and end in a direction opposite or otherwise different from that of the second scanning pattern 94 illustrated in FIG. 6B. Additionally, the width $X_3$ of third ablation layer 100 is less than the width $X_2$ of the second ablation layer 80, and the length $Y_3$ of the third ablation layer 100 is greater than the width $Y_2$ of the second ablation layer 80.

Figure 6D:
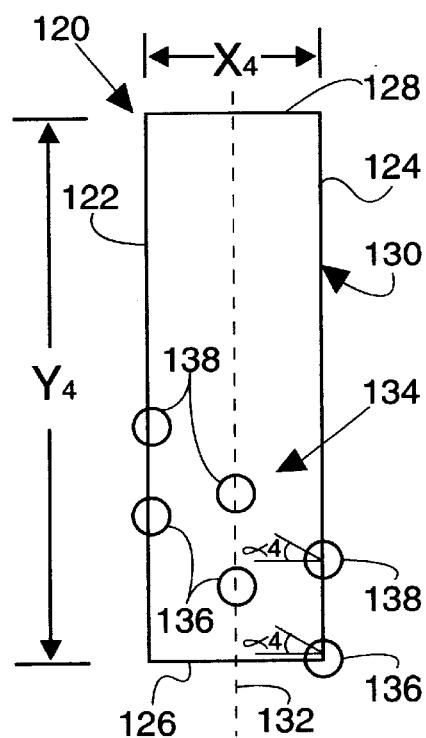

FIG. 6D shows a fourth ablation layer 120 having a pair of opposing sides 122 and 124 defining the width $X_4$ of the fourth ablation layer 120, and opposing ends 126 and 128 defining the length $Y_4$ of the fourth ablation layer 120. The width $X_4$ and length $Y_4$ define a rectangular zone 130 having an axis of symmetry which is represented by the dashed line 132. The rectangular zone 130 is also the boundary of the fourth ablation layer 120.

FIG. 6D also shows a fourth scanning pattern 134 for the fourth ablation layer 120 determined in accordance with the principles of the present invention. The fourth scanning pattern 134 includes laser pulses 136 and 138. The lasers pulses 136 and 138 start and end on the boundary 130 of the fourth ablation layer 120. For example, laser pulses 136 start on the side 124 and end of the side 122. The laser pulses 138 also start on the side 124 and also end on the side 122. Since the distance between the pulses 136 and 138 are fixed and the width $X_4$ and length $Y_4$ are known, a rotation angle $\alpha_4$ can be calculated in accordance with the principles of the present invention such that the starting and ending pulses will lie substantially on the boundary 130 of the fourth ablation layer 120. This will result in a symmetric distribution of the pulses 136 and 138 about the axis 132 which forces all of the pulses 136 and 138 to be centered about the axis 132.

The fourth scanning pattern 134 represented by the pulses 136 and 138 illustrated in FIG. 6D may begin and end in a direction opposite or otherwise different from that of the third scanning pattern 114 illustrated in FIG. 6C. Additionally, the width $X_4$ of the fourth ablation layer 120 is less than the width $X_3$ of the third ablation layer 100, and the length $Y_4$ of the fourth ablation layer 120 is greater than the width $Y_3$ of the third ablation layer 100.

The pulses in subsequent layers may be controllably overlapped to provide a smoother corneal surface. Each pulse generally ablates a substantially bowl-shaped region of the corneal tissue with the center of the region being the deepest portion and the perimeter being the shallowest. For example, if two pulses were exactly overlapped, the result would be a region that substantially covered an area of a single laser ablation pulse but which is approximately twice as deep as the original pulse. The center region of pulses of one layer may be overlapped with the outside regions of pulses of another layer to provide a smoother overall ablation. Thus, by controlling both the number of pulses per layer and the number of layers, the depth of ablation can be controlled with high accuracy.

As discussed above with reference to the first, second, third and fourth scanning patterns 74, 94, 114, and 134, all of the pulses associated with the scanning patterns 74, 94, 114, and 134 may not fit neatly on the various boundaries. Accordingly, in order to determine a complete scanning pattern for a given ablation layer in such a region, reference is made to FIG. 7.

Figure 7:
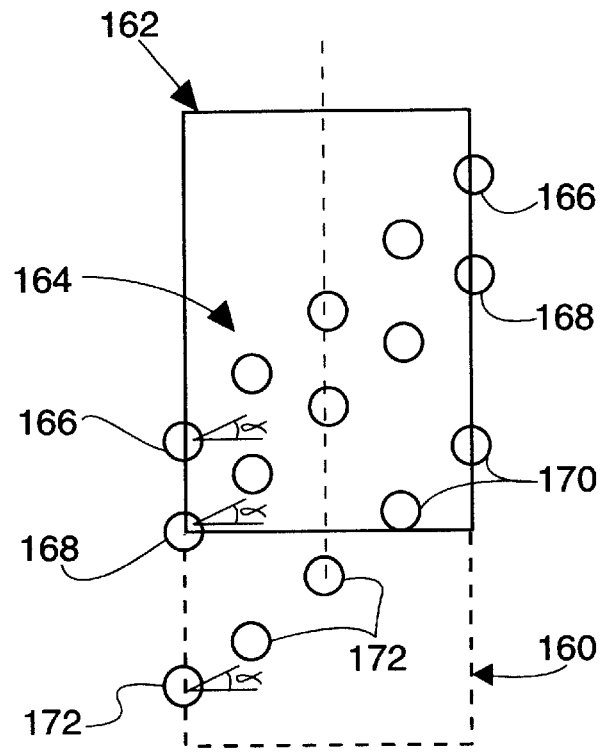
FIG. 7 illustrates a representative layer having an actual boundary and a representative extension associated therewith illustrated in phantom constructed in accordance with the present invention.

FIG. 7 shows an imaginary extension 160 of an actual boundary 162. The imaginary extension 160 is used to determine a scanning pattern 164 for the boundary 162. The scanning pattern 164 includes laser pulses 166, 168, and 170. As discussed, the present invention provides laser pulses 164 and 166 which start and end on the boundary 162. However, in accordance with the method of the present invention, only the laser pulses 170 which occur on or within the boundary 162 actually occur. The pulses 172 which appear in the imaginary extension 160 do not actually occur but are merely used by the computer system 18 to determine the scanning pattern 164. In this manner the entire scanning pattern 164 for the boundary 162 may be determined.

Figure 8:
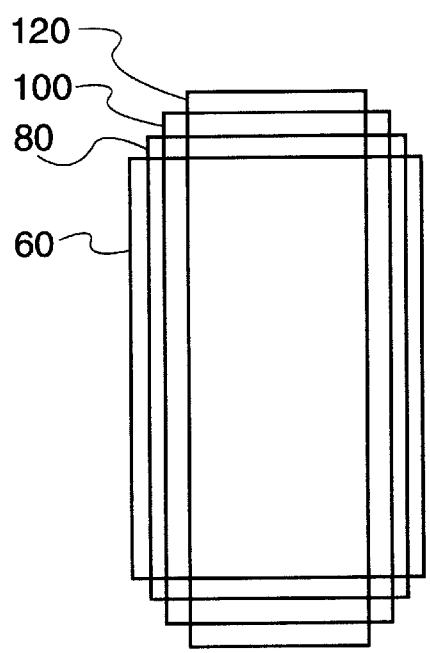
FIG. 8 illustrates a first method of providing smooth transition at the ends of the layer of an overlapping top view of the layers of FIGS. 6A–6D constructed in accordance with the present invention in which the ends of the layer are not required to be rounded so long as the narrower layers are longer than the wider layers.

FIG. 8 shows another aspect of the present invention, wherein subsequent layers have a progressively decreasing width to provide a more accurate ablation.

In particular, four overlapping ablation layers 60, 80, 100, and 120 as described with respect to FIGS. 6A to 6D. The overlapping ablation layers 60, 80, 100, and 120 have different dimensions to achieve the cylindrical surface 48 of a cylindrical-shaped ablation, e.g., as shown in FIGS. 3a and 3b. Similarly, the smooth transition regions 50 and 52 (e.g., FIG. 3c) may be formed by progressively increasing the lengthwise ends of subsequent ablation layers 60, 80, 100, 120 as shown in FIG. 8. Thus, as pointed out previously with reference to FIGS. 6A–6D, in general, $X_1 > X_2 > X_3 > X_4$, and $Y_1 < Y_2 < Y_3 < Y_4$. As a result of providing an initial layer followed by each succeeding layer being longer and narrower than the previous layer, the final ablation will have corners which are generally curved.

Figure 9:
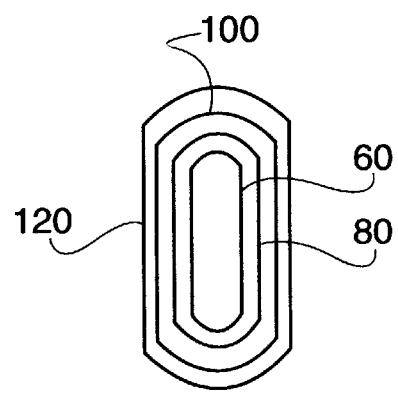
FIG. 9 illustrates a second method of providing smooth transition at the ends of the layer constructed in accordance with the present invention in which each rectangular layer is rounded at the ends with the wider layers being longer than the narrower layers.

Another method for providing transition regions at the ends of the ablation layers is best illustrated in FIG. 9. In FIG. 9, each generally rectangular ablation layer is rounded at the ends with wider layers being longer than narrower layers.

The laser device 10 (FIG. 1) in accordance with the principles of the present invention is operable to perform the aforementioned procedures according to a program which may be loaded into the computer system 18 of such device 10. An exemplary flow chart of such a novel program 200 is illustrated in FIG. 10.

Figure 10:
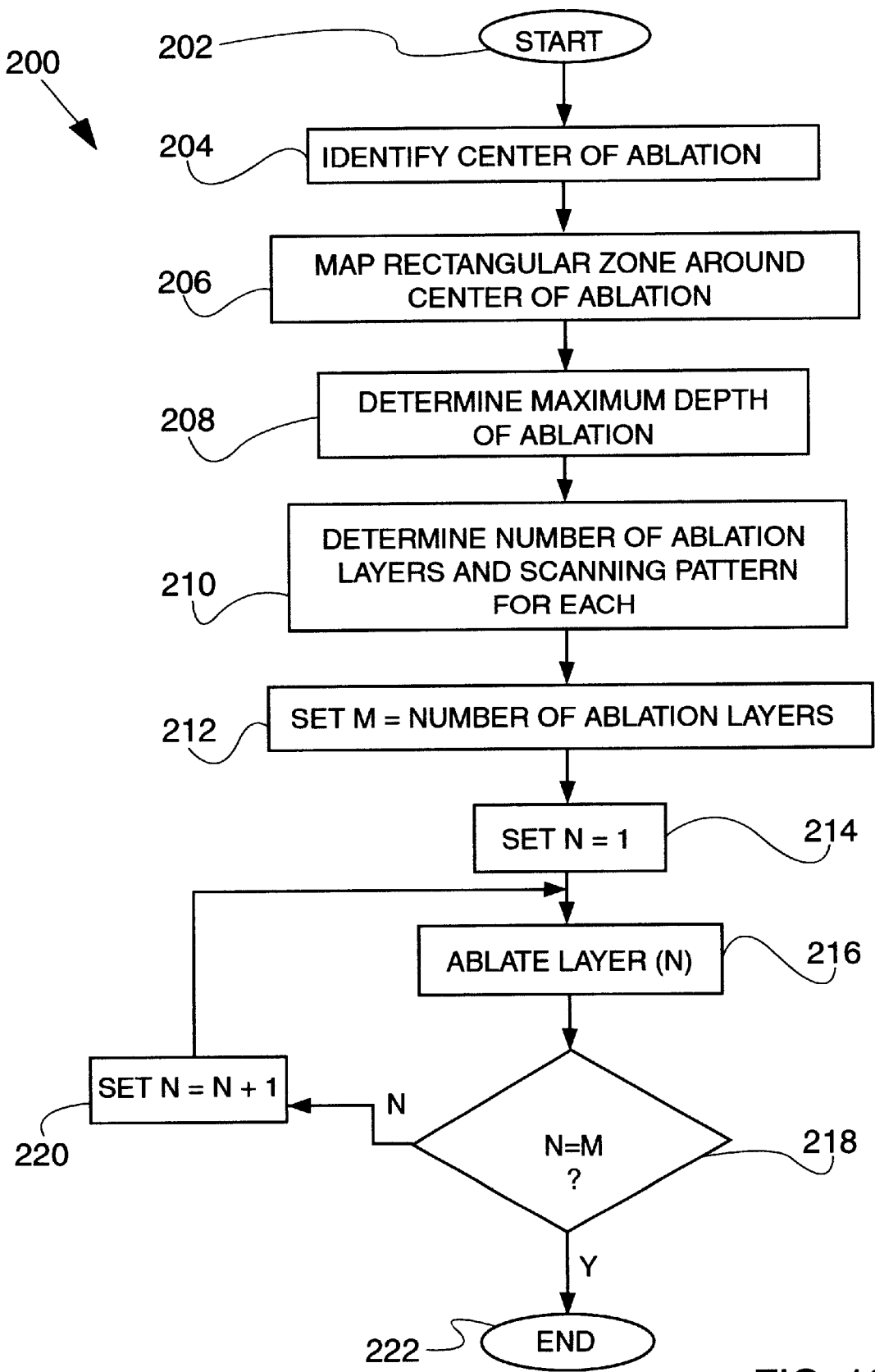
FIG. 10 is a flow chart of a program utilized to control the operation of the device illustrated in FIG. 1 to re-profile the surface an eye constructed in accordance with the present invention.

In FIG. 10, the control of the program 200 starts at a start step 202 and proceeds to a step 204 which identifies the center of the ablation zone. Once the center is identified, the next step encountered is a step 206 in which a rectangular zone is mapped around the center of the ablation. The program 200 passes to a step 208 which calculates the maximum depth of the ablation. The next step is a step 210 where the number of layers requiring ablation is determined and also the scanning pattern for each of the layers is also determined. Once the number of layers to be ablated and the scanning patterns have been calculated, control of the program 200 proceeds to a step 212 in which a variable M is set equal to the total number of layers to be ablated, which was determined in the previous step 210. Control of the program 200 next passes to a step 214 in which a variable N is set equal to 1. The next step is a step 216 in which ablation of an Nth layer occurs. After the Nth layer has been ablated by the previously determined scanning pattern, the program 200 proceeds to a step 218 in which a decision is made as to whether the variable N (i.e., the layer number which was just ablated) is equal to the variable M (i.e., the total number of layers to be ablated). If N does not equal M, the program 200 branches to a step 220 in which the layer number is incremented by one.

The program 200 then loops back to step 216 to continue ablating subsequent layers until the last layer has been ablated as determined in step 218, wherein the value of N becomes equal to the value of M. Once the condition of N equal to M (i.e., all layers have been ablated) is met, the program 200 ends at a step 222.

There has thus been shown and described herein a novel device and method for correcting a simple astigmatism by laser ablation which fulfills the various objects and advantages sought therefor. The device and method of the present invention corrects simple astigmatism by more accurately creating a cylinder-shape correction in a cornea by tissue ablation. Additionally, the device and method of the present invention increases the accuracy of the width of each ablated layer, and improves the centration accuracy of each ablated layer. Furthermore, the device and method of the present invention ablate the total depth of the corneal tissue more accurately.

The foregoing exemplary descriptions and the illustrative embodiments of the present invention have been explained in the drawings and described in detail, with varying modifications and alternative embodiments being taught. While the invention has been so shown, described and illustrated, it should be understood by those skilled in the art that equivalent changes in form and detail may be made therein without departing from the true spirit and scope of the invention, and that the scope of the present invention is to be limited only to the claims appended hereto. Moreover, the invention as disclosed herein may be suitably practiced in the absence of the specific elements which are disclosed herein.

What is claimed is:

1. A method for correcting astigmatism in an eye, said method comprising:

scanning an ablating laser beam in a predetermined pattern across an ablation zone of said eye to form a cylindrical-shaped ablation in a cornea of said eye; and over ablating a transition region in each end of said cylindrical-shaped ablation.

2. The method for correcting astigmatism in an eye according to claim 1, wherein:

said over ablating forms a trough in each end of said cylindrical-shaped ablation.

3. The method for correcting astigmatism in an eye according to claim 1, wherein:

said over ablating is performed with said scanning said ablating laser beam in said predetermined pattern.

4. The method for correcting astigmatism in an eye according to claim 1, wherein:

said over ablating is performed subsequent to said scanning said ablating laser beam in said predetermined pattern.

* * * * *